United States Patent [19]

Price et al.

[11] 4,195,642
[45] Apr. 1, 1980

[54] WEARABLE HEART RATE MONITOR

[75] Inventors: Edward G. Price, Salt Lake City; Lewis C. Rasmussen, Bountiful, both of Utah

[73] Assignee: Beehive International, Salt Lake City, Utah

[21] Appl. No.: 866,334

[22] Filed: Jan. 3, 1978

[51] Int. Cl.² .............................. A61B 5/02
[52] U.S. Cl. .................................... 128/689
[58] Field of Search ............ 128/2.05 P, 2.05 R, 128/2.05 T, 2.06 A, 2.06 F, 2.06 T

[56] References Cited

U.S. PATENT DOCUMENTS

| | | | |
|---|---|---|---|
| 3,593,704 | 7/1971 | Schwab | 128/2.05 P |
| 3,646,931 | 3/1972 | Phelps et al. | 128/2.05 P |
| 3,993,047 | 11/1976 | Peek | 128/2.05 T |
| 4,063,551 | 12/1977 | Sweeney | 128/2.05 T |
| 4,086,916 | 5/1978 | Freeman et al. | 128/2.05 T |

OTHER PUBLICATIONS

Atherton, "Medical and Biological Engineering", vol. 13, No. 5, Sep. 1975, pp. 669-673.

*Primary Examiner*—William E. Kamm
*Attorney, Agent, or Firm*—Thorpe, North & Gold

[57] ABSTRACT

A wearable heart rate monitor includes a wrist cuff or strap suitable for being placed about the wrist of a person, a display housing mounted on the wrist cuff, a pressure transducer element also mounted on the wrist cuff at a position to cover the radial artery when the wrist cuff is placed about the wrist, and logic circuitry disposed in the display housing for producing an indication of the pulse rate of the individual wearing the wrist cuff. The pressure transducer element detects expansion and contraction of the radial artery and applies a signal to the logic circuitry which then produces a visual display of the pulse rate.

2 Claims, 3 Drawing Figures

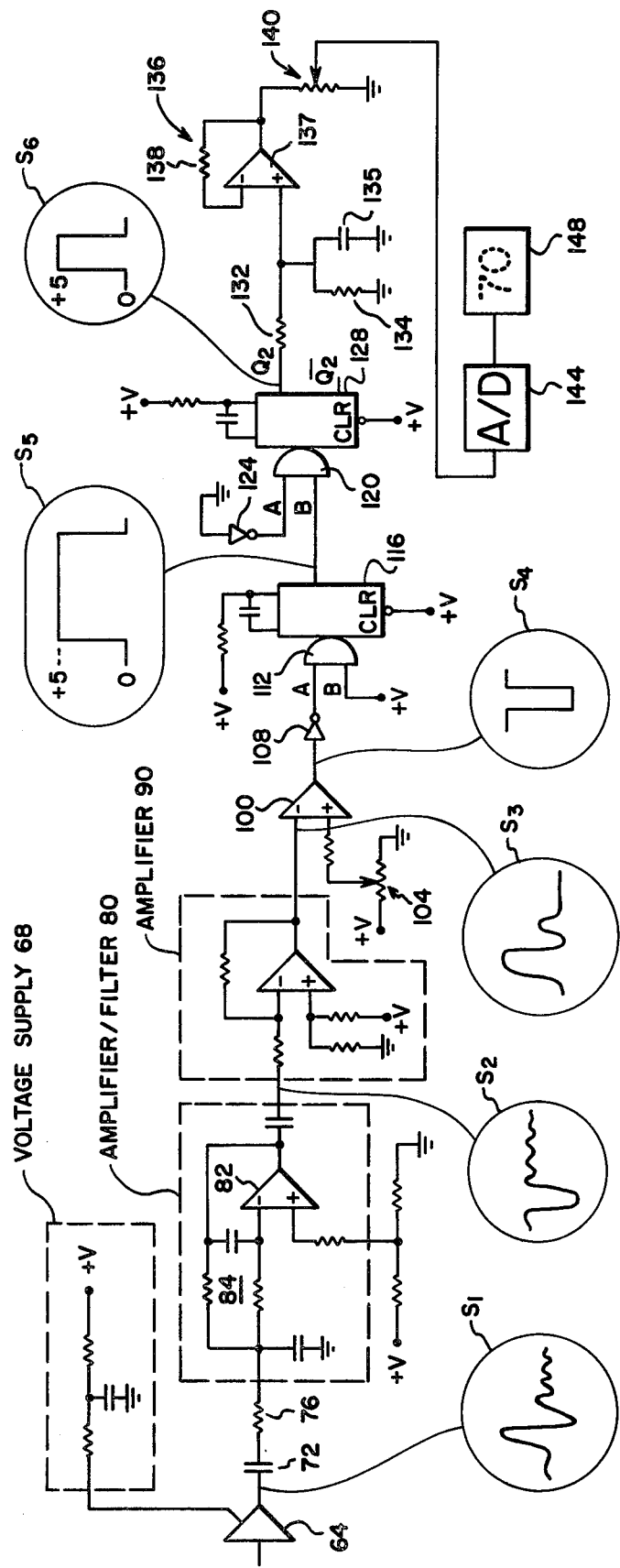
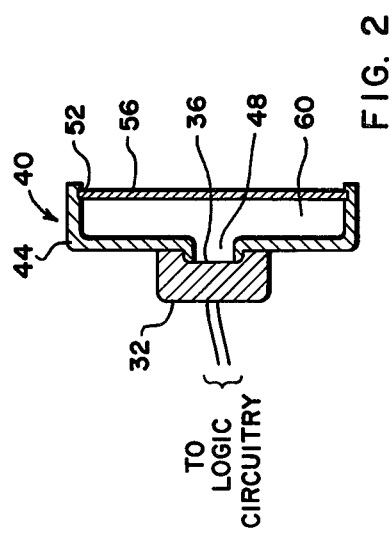
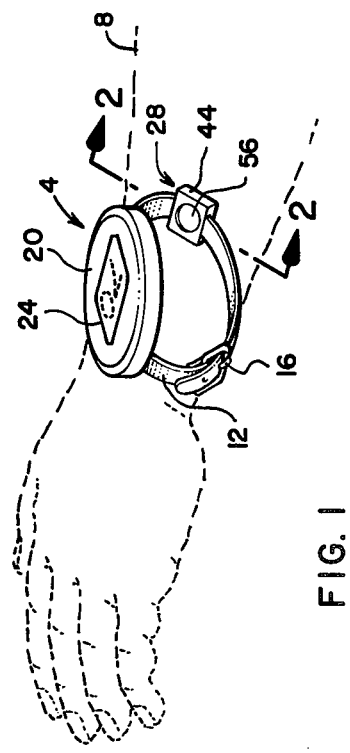
FIG. 3
FIG. 2
FIG. 1

WEARABLE HEART RATE MONITOR

BACKGROUND OF THE INVENTION

This invention relates to apparatus for detecting and providing an indication of the pulse rate of a human, and more particularly to a lightweight, compact structure which may be worn on the wrist of a person.

The conventional method of measuring the heartbeat or pulse rate of a patient is for the person taking the measurement to place his finger over an artery of the patient and then count the number of pulses which occur over some predetermined period of time, usually a minute. Of course, the measurement may be taken over a shorter period of time and then the pulse count multiplied by an appropriate multiplying factor to obtain the number of pulses per minute (the usual form in which a patient's pulse rate is given). Also, a stethoscope or other suitable measuring device is sometimes used to more accurately detect the heartbeat, but again the counting of the number of pulses is usually done by the person making the measurement.

The principal drawback of the above-described method is that it is time consuming since it usually requires counting a patient's pulses over some reasonable period of time up to a minute. Additionally, since human intervention is required, errors can occur in the measurement of the pulse rate.

There have been a number of devices proposed for automatically measuring a person's pulse rate including those disclosed in U.S. Pat. Nos. 3,646,931, 3,978,848, 3,535,067 and 3,661,147. These patents all disclose various arrangements for detecting either pulse rate, blood pressure, or both, and for producing some type of display thereof. Although these arrangements appear to be capable of determining pulse rate, none provides the convenience of a pulse rate monitor which may be conveniently worn by a patient and provide a pulse rate indication at any time the patient desires in a simple, accurate and economical fashion.

SUMMARY OF THE INVENTION

It is an object of the invention to provide a compact device suitable for being worn by a person for measuring heartbeat rate or pulse rate.

It is also an object of the present invention to provide such a device which can produce a visual indication of a person's pulse rate without the need for counting over any significant number of pulses.

It is a further object of the present invention to provide such a device which is capable of providing an indication of the pulse rate at any time the user desires.

It is still another object of the present invention to provide such a device which requires relatively simple and inexpensive circuitry for producing the pulse rate indication.

The above and other objects are realized in an illustrative embodiment of a heart rate monitor which includes a wrist cuff for placement about the wrist of a person, a display housing mounted on the wrist cuff, a pressure transducer also mounted on the wrist cuff at a location to be positioned over the radial artery of the person when the wrist cuff is placed on the person's wrist, and logic circuitry mounted in the display housing for producing an indication of the person's heart rate in response to signals received from the pressure transducer. The pressure transducer might illustratively include a solid state pressure responsive device for producing an electrical signal in response to pressure being applied to an exposed surface area of the device, and a diaphragm housing having a first opening disposed over the exposed surface area of the solid state pressure device, and a second opening which is larger than the first opening. The pressure transducer might also include a diaphragm placed over the second opening for detecting the expansion and contraction of a person's artery. This expansion and contraction is magnified by the diaphragm to enable the solid state pressure responsive device to better detect the occurrence of pulses in the artery. The diaphragm vibrates to produce pressure variations which are detected by the pressure responsive device and this, in turn, produces an electrical signal whose amplitude is proportional to the pressure applied to the exposed surface area. The solid state pressure responsive device applies the signal to the logic circuitry which then produces an indication of the person's pulse or heart rate.

Because the heart rate monitor is adapted for wearing on a person's wrist, an indication of the person's heart rate can be made available at any time the person desires. Thus, during an activity requiring physical exertion, the person can continually monitor his heart rate and adjust his activity accordingly.

BRIEF DESCRIPTION OF THE DRAWINGS

The above and other objects, features and advantages of the present invention will become apparent from a consideration of the following detailed description presented in connection with the accompanying drawings in which:

FIG. 1 shows a perspective view of a wearable heart rate monitor made in accordance with the principles of the present invention;

FIG. 2 shows a side, cross-sectional view of the pressure transducer apparatus of the heart rate monitor of FIG. 1; and FIG. 3 is a schematic diagram of one illustrative embodiment of logic circuitry suitable for use in the present invention.

DETAILED DESCRIPTION

Referring to FIG. 1 there is shown a wearable heart rate monitor 4 positioned on a person's wrist (which is indicated by dotted line 8). The monitor includes a flexible wrist cuff or band 12 constructed similar to a watch band. A buckle 16 is attached to the cuff for enabling joining two free ends of the cuff together and for enabling variation in the size of the loop formed by the cuff to accommodate different size wrists. Other means for securing the ends of the cuff 12 together, such as the use of velcro strips, could also be provided.

Mounted on the outside surface of the wrist cuff 12 is a display housing 20 having an opening 24 in the top wall thereof. The housing 20 is mounted on the cuff 12 at a location such that when the cuff is placed about the wrist of the person, the housing is positioned on the top of the wrist. The mounting of the housing may be by adhesives, brackets formed in the housing through which the cuff 12 is threaded, etc. The housing 20 is provided to contain and house logic circuitry (to be described later) for computing the heart rate and for presenting a visual display thereof through the opening 24. This housing could be of any shape but generally need not be any larger than a conventional wrist watch housing.

Also mounted on the wrist cuff 12 is a pressure transducer 28. The transducer 28 is mounted on the inside surface of the cuff 12 by an adhesive or other suitable attaching means at a location to be positioned over the radial artery of the person's wrist on whom the wrist cuff is placed. (The radial artery is on the inside and slightly to one side of a person's wrist.) As will be described in greater detail later, the pressure transducer 28 detects the contraction and expansion of the radial artery and produces an electrical signal in response thereto. This electrical signal is applied to logic circuitry contained in the housing 20 for use in calculating the pulse or heart rate of the person. An indication of this rate is then visually displayed through the opening 24 of the housing 20 using light emitting diodes, liquid crystal display circuitry, or the like.

FIG. 2 shows a cross-sectional view of the pressure transducer 28 of FIG. 1. The pressure transducer includes a solid-state pressure responsive device 32 capable of producing electrical signals in response to the application of pressure to a certain exposed surface area 36 of the device. Such a device might illustratively be the so-called electret condenser microphone made by Primo Company, Ltd. of Tokyo, Japan. This device produces an output signal whose amplitude is proportional to the pressure applied to the exposed surface area 36. Further description of the device is found in Primo Co., Ltd., Specification for Electret Condenser Microphone Cartridge, Model No. EM-38B, Drawing No. 32330.

The pressure transducer of FIG. 2 also includes a diaphragm housing 40 formed with side walls 44 and having a first opening 48 located at one end of the housing and a second larger opening 52 located at the opposite end. The housing 40 is attached by adhesive to the device 32 so that the smaller opening 48 in the housing is positioned over the exposed surface area 36 of the device. The larger opening 52 is covered by a flexible, conventional diaphragm 56. The device 32 and diaphragm 56 are attached over respective openings in the housing 40 in a suitable manner to define a sealed chamber 60 within the housing. It is thus clear that when the diaphragm 56 is moved, a variation in pressure in the chamber 60 occurs and this pressure variation is detected by the device 32 via the exposed surface area 36.

In use, the pressure transducer of FIG. 2 is positioned in the wrist cuff 12 (FIG. 1) so that the diaphragm 56 is placed over the radial artery of the person's wrist. Any contraction or expansion of the radial artery causes the adjacent superficial skin to move, and thus the diaphragm 56 to also move. The diaphragm movement, in turn, is detected by the pressure responsive device 32. In practice, any contraction or expansion of the radial artery causes the diaphragm 56 to vibrate and this, in turn, causes the device 32 to produce an oscillatory signal whose magnitude nevertheless is proportional to the magnitude of movement of the diaphragm 56 and thus to the magnitude of the contraction or expansion of the artery.

The electrical signal produced by the solid state pressure responsive device 32 of FIG. 2 is applied to logic circuitry shown schematically in FIG. 3. In particular, the pressure transducer of FIG. 2 is shown symbolically as element 64 of the circuitry of FIG. 3. A voltage supply 68 is coupled to the transducer 64 to supply the transducer with power. The output line of the transducer is coupled by way of a series connection of a capacitor 72 and a resistor 76 to an amplifier/filter circuit 80. The amplifier filter circuit 80 includes an operational amplifier 82 and a filter circuit 84 coupled together to both amplify (and invert) the signal supplied by the transducer 64 and to filter out the higher frequency components (e.g., those above 50 Hz) of the signal.

The output of the amplifier/filter 80 is supplied to a supplementary amplifier 90 which further amplifies the signal to a desired level, inverts the signal and eliminates unwanted components from the signal. The amplifier 90 includes an operational amplifier and other conventional components as shown. The output of the amplifier 90 is supplied to the inverting input terminal of an operational amplifier 100, which serves as a voltage comparator. The noninverting input terminal of the amplifier 100 is coupled to the wiper arm of a potentiometer 104. When the signal level on the inverting input terminal of the operational amplifier exceeds the signal level supplied to the noninverting input terminal, a zero voltage level signal is produced by the amplifier. Thus, the operational amplifier 100 normally produces a high level output signal until the signal applied by the supplementary amplifier 90 to the inverting input terminal exceeds the level on the noninverting input terminal. When this occurs, a zero voltage level pulse is produced by the amplifier 100 and applied via an inverter 108 to input line A of an AND gate 112 which is coupled to a monostable multivibrator 116. The pulse is inverted by the inverter 108 to a positive voltage level pulse and this, together with the positive voltage level input supplied over input line B of the AND gate 112, causes the AND gate to trigger the monostable multivibrator 116.

When triggered, the monostable multivibrator 116 is caused to produce a positive voltage level output signal which is applied to an input line B of an AND gate 120. The duration of the output signal from the monostable multivibrator 116 is of a fairly long duration, for example, 0.4 seconds. The AND gate 120 includes another input line A which is connected via an inverter 124 to a ground level voltage source. The inverter 124 inverts the signal of the ground level voltage source to a positive signal and this, together with the signal produced by the monostable multivibrator 116, enables the AND gate 120 causing it to trigger another monostable multivibrator 128.

The monostable multivibrator 128, in turn, produces a positive voltage level, constant width output pulse of fairly short duration, for example, 50 milliseconds, which is supplied via a resistor 132 to a tachometer circuit 136. The tachometer circuit 136 operates to produce an output voltage level whose magnitude is proportional to the rate at which the constant width pulses are received from the monostable multivibrator 128. The output of the tachometer circuit 136 is supplied via a potentiometer 140 to an analog-to-digital inverter 144 which converts the analog signal to a digital signal for application to a display device 148. The display device then displays an indication of the value of the received digital signal and this represents the heart rate of the person being monitored. This indication is displayed through the opening 24 of the display housing 20. The display device might illustratively be the field-effect liquid crystal display manufactured by Beckman Instruments.

In operation, the transducer 64 produces an oscillatory signal such as shown at $S_1$ as a result of expansion of the radial artery of the person. The signal comprises one predominant pulse and then a plurality of smaller oscillations. The oscillations occur because of the vibrations of the diaphragm 52 of the pressure transducer. The signal from the transducer 64 is applied to the amplifier/filter 80 which is adapted to invert the incoming signal and amplify it by a factor of 10 for all frequencies up to 50 hertz. Beyond that frequency the signal is attenuated approximately 6 db/octave, and thus the unwanted higher frequency signals are inhibited from proceeding through the network. This amplifier/filter circuit, which is known as a second order, infinite gain, multiple feedback low pass filter, is a well known arrangement.

The signal from the amplifier/filter (shown graphically at $S_2$) is applied to the supplementary amplifier 90 which inverts the signal and further amplifies it (especially the predominant pulse) to a desired level. This amplifier circuit is also a well known arrangement.

The output of the supplementary amplifier is applied to the operational amplifier 100 which produces a zero level voltage pulse such as shown at $S_4$ when the level of the signal on the inverting input terminal exceeds the level of the signal on the noninverting input terminal. In other words, the amplifier 100 produces the signal $S_4$ on receipt of the first oscillation of sufficient magnitude to trigger the amplifier (this first oscillation is the predominant pulse of the signal produced by the transducer). The setting of the potentiometer 104 determines magnitude of the signal necessary to trigger the amplifier 100 and this value may be varied, of course, by adjustment of the potentiometer. The output of the amplifier 100 is maintained at the zero voltage level so long as the signal on the inverting input terminal of the amplifier exceeds the magnitude of the signal on the noninverting input thereof.

The signal $S_4$ is applied via the inverter 108 to enable the AND gate 112 and cause the monostable multivibrator 116 to produce a positive level voltage signal such as shown at $S_5$. The duration of this signal is sufficiently long to, in effect, lock out any trailing pulses or oscillations produced by the pressure transducer other than the leading predominant pulse. The multivibrator 116 produces its output upon generation of the leading edge of the predominant pulse so that any pulses or oscillations occurring within 0.4 seconds after generation of the $S_5$ signal are locked out. The leading edge of the signal produced by the monostable multivibrator 116 enables the AND gate 120 which in turn triggers the multivibrator 128 to produce a pulse signal such as shown at $S_6$. These signals are applied to the tachometer circuit 136 which includes a resistor 134 and a capacitor 135 connected in parallel between the noninverting input of an operational amplifier 137 and ground. Another resistor 138 is connected between the output of the operational amplifier 137 and the inverting input thereof.

The pulses produced by the multivibrator 128 serve to charge the capacitor 135. The capacitor discharges via the resistor 134, with the RC time constant being chosen so that the pulses from the multivibrator 128 maintains a fairly constant level charge on the capacitor. The operational amplifier 137 presents a high impedance to the capacitor and acts as a unit gain buffer so that the output of the amplifier 137 is substantially a reflection of the input voltage level on the noninverting input of the amplifier. The feedback connection through resistor 138 is provided so that the voltage level on the inverting input of the amplifier 137 is maintained lower than the voltage level on the noninverting input.

The tachometer circuit 136 continually produces an output voltage signal as long as pulses are being received from the multivibrator 128 and so a continuous pulse or heart rate reading is maintained. Of course, if the rate at which pulses are produced by the multivibrator 128 increases, then the output level of the tachometer circuit 136 increases and vice versa.

The voltage signal produced by the tachometer 136 is applied via the potentiometer 140 to the analog-to-digital converter 144 which converts the signal to a digital signal for application to the display device 148. The potentiometer 140 is provided to enable calibration of the display device 148.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Pulse rate determination apparatus comprising
 transducer means for producing a signal in response to the heartbeat of a person,
 means for producing a pulse having a fixed width in response to each signal produced by said transducer means, and
 tachometer circuit means for producing a voltage signal whose amplitude is proportional to the rate at which said pulses are produced, said tachometer circuit means including
  operational amplifier means having an inverting input and noninverting input,
  said noninverting input being coupled to said pulse producing means to receive pulses therefrom,
  first resistance means coupling the output of said operational amplifier means to said inverting input,
  capacitor means,
  second resistance means connected in parallel with said capacitor means, and
  means coupling one end of the parallel connection of said capacitor means and second resistance means to the noninverting input of said operational amplifier means and the other end to ground, and means responsive to said voltage signal for producing an indication of the person's heart rate.

2. Apparatus as in claim 1 wherein said indication producing means comprises
 analog-to-digital converter means for converting said voltage signal into a digital signal whose value is proportional to the amplitude of the voltage signal, and
 display means for producing a visual display of the value of said digital signal.

* * * * *